United States Patent
Kim et al.

(10) Patent No.: US 9,028,881 B2
(45) Date of Patent: May 12, 2015

(54) COMPOSITION FOR PREVENTING AND TREATING HANGOVER

(75) Inventors: Bum-Sik Kim, Anyang (KR); Kang-Pyo Lee, Seoul (KR); Masaharu Nakaura, Fukuyama (JP); Nobuaki Ohto, Fukuyama (JP)

(73) Assignee: CJ Cheiljedang Corporation, Seoul (KR)

( * ) Notice: Subject to any disclaimer, the term of this patent is extended or adjusted under 35 U.S.C. 154(b) by 915 days.

(21) Appl. No.: 11/913,430

(22) PCT Filed: May 2, 2005

(86) PCT No.: PCT/KR2005/001275
§ 371 (c)(1),
(2), (4) Date: Nov. 2, 2007

(87) PCT Pub. No.: WO2006/118358
PCT Pub. Date: Nov. 9, 2006

(65) Prior Publication Data
US 2009/0130238 A1 May 21, 2009

(51) Int. Cl.
*A61K 35/00* (2006.01)
*A61K 36/738* (2006.01)
*A23L 1/30* (2006.01)
*A61K 36/52* (2006.01)
*A61K 36/62* (2006.01)

(52) U.S. Cl.
CPC .............. *A23L 1/3002* (2013.01); *A61K 36/52* (2013.01); *A61K 36/62* (2013.01); *A61K 36/738* (2013.01)

(58) Field of Classification Search
None
See application file for complete search history.

(56) References Cited

FOREIGN PATENT DOCUMENTS

| KR | 2000-0021322 A | | 4/2000 |
|---|---|---|---|
| KR | 2003004288 A | * | 1/2003 |
| KR | 2003-0031729 A | | 4/2003 |
| KR | 2003-0079104 A | | 10/2003 |
| KR | 2004-0026175 A | | 3/2004 |
| KR | 0436428 B1 | | 6/2004 |
| KR | 2004-0065134 A | | 7/2004 |
| KR | 2005-0104036 A | | 11/2005 |
| WO | WO 02080946 A1 | * | 10/2002 |
| WO | 2004/035040 | | 4/2004 |

OTHER PUBLICATIONS

Masako et al, Hangover susceptibility in relation to aldehyde dehydrogenase-2 genotype, alcohol flushing, and mean corpuscular volume in Japanese workers, Alcoholism, clinical and experimental research, (Jul. 2005) vol. 29, No. 7, pp. 1165-1171.*
Foster et al, Alcohol consumption in the new millennium—Weighing up the risks and benefits for our health, Nutrition Bulletin, (Dec. 2006) vol. 31, No. 4, pp. 286-331.*
Haas et al, Hangover symptoms after alcohol consumption: Epidemiology, risk factors and pathophysiology]. Katersymptome nach alkoholkonsum: Epidemiologie, risikofaktoren und pathophysiologie, Sucht, (Oct. 2006) vol. 52, No. 5, pp. 317-326.*
Wendy et al, Development and initial validation of the Hangover Symptoms Scale: prevalence and correlates of Hangover Symptoms in college students, Alcoholism, clinical and experimental research, (Sep. 2003) vol. 27, No. 9, pp. 1442-1450.*
Tamara et al, Genetic associations of alcohol dehydrogenase with alcohol use disorders and endophenotypes in white college students, Journal of abnormal psychology, (Aug. 2005) vol. 114, No. 3, pp. 456-465.*
Newlin et al, Sons of alcoholics report greater hangover symptoms than sons of nonalcoholics: a pilot study, Alcoholism, clinical and experimental research, (Oct. 1990) vol. 14, No. 5, pp. 713-716.*
Wall et al, Hangover symptoms in Asian Americans with variations in the aldehyde dehydrogenase (ALDH2) gene, Journal of studies on alcohol, (Jan. 2000) vol. 61, No. 1, pp. 13-17.*
Brekhman, "Pharmacological Investigation of Glycosides from Ginseng and Eleutherococcus," Lloydia, (1969) 45-51, 32.
Sen, R. et al, Mechanism of Anti-Stress Activity of Linn, Eugenol and in Experimental Animals, Indian J. Exp Biol, (1992) 592-596, 30.
English Translation of Abstract; Korean Publication No. KR 2000-0021322; Applicant: Cho, Won Ki; Published Apr. 25, 2000 (Abstract Only) (1 Pg).
English Translation of Abstract; Korean Publication No. KR 2004-0026175; Applicant: Kyunghee University; Published Mar. 30, 2004 (Abstract Only) (2 Pgs).
English Translation of Abstract; Korean Publication No. KR 2003-0079104; Applicant: Purimed Co., Ltd; Published Oct. 10, 2003 (Abstract Only) (1 Pg).
English Translation of Abstract; Korean Publication No. KR 2003-0031729; Applicant: Wonkwang Educational Foundation; Published Apr. 23, 2003 (Abstract Only) (1 Pg).
Bhisagacarya HPV, "Vagabhata; Astanga Hrdaya, Formulation Madatya Cikitsa RS23/596D", Ayurveda, 8th Edition 1998, p. 634.
Biochem. Pharmacol., 1972, 21:594-600.
Ling et al., J. Agric. Food Chem. 2005, 4, 53(7):2441-2445.
Yoshido et al., Chem. Pharm. Bull. 1987, 35(5):1817-1822.

* cited by examiner

*Primary Examiner* — Qiuwen Mi
(74) *Attorney, Agent, or Firm* — Cesari and McKenna, LLP

(57) ABSTRACT

There is provided a composition for preventing and treating katzenjammers comprising at least one extract selected from the group consisting of a *Rosa roxburghii* extract, an *Engelardtia chrysolepsis* HANCE extract, a *Nelumbo nucifera* extract and a combination thereof as an active ingredient.

6 Claims, 3 Drawing Sheets

COMPOSITION FOR PREVENTING AND TREATING HANGOVER

TECHNICAL FIELD

The present invention related to a composition for preventing and treating katzenjammers, and more particularly, to a composition comprising herb extracts for preventing and treating katzenjammers.

BACKGROUND ART

People undergo various stress everyday. People intend to escape stress, but this task is nearly impossible. To prevent stress from building up, various activities such as sleeping, overeating, exercise, smoking, etc. are conducted. Drinking is also included in such activities.

Due to frequent dining and receptions, occasions to drink are increasing. However, people suffer from side effects of drinking after continuous drinking. Such side effects of drinking include a heavy feeling in the head, a headache, a pain in one's insides and a parched mouth. These symptoms are referred to as a katzenjammer. A katzenjammer results from toxic action of ethanol or acetaldehyde. When the toxic action of ethanol or acetaldehyde lasts, fatigue, abdominal distension, emesis, etc. occur.

In normal metabolism of ethylalcohol, ethylalcohol introduced into the body is absorbed by the stomach or the small intestines and transferred to the liver through blood vessels. Liver cells have alcohol dehydrogenase (ADH) which oxidizes alcohol to produce acetaldehyde. Acetaldehyde is metabolized to produce acetic acid by acetaldehyde dehydrogenase (ALDH) in liver cells and transferred to muscles or fat tissue throughout the whole body, and is finally decomposed to carbon oxide and water. The ALDH is divided into ALDH type II, which initiates oxidation even in a low concentration of acetaldehyde, and ALDH type I, which does not function in a low concentration of acetaldehyde. Since Eastern people are generally deficient in ALDH (II), the oxidation of acetaldehyde is slower in Eastern people than in Western people. Non-oxidized acetaldehyde and/or ethanol interfere with the normal metabolism, thereby causing various katzenjammer symptoms.

Meanwhile, ethanol is a main ingredient of alcoholic drink and physically and mentally affects the human body. Thus, the metabolism and toxicity of ethanol have been broadly studied. Intaken ethanol is absorbed by digestive tracts including the small between 20 and 120 minutes after drinking. The absorbed ethanol is metabolized in all organs including the liver. About 10% of the absorbed ethanol is excreted through the breath, perspiration, or urination and most of the remaining portion is decomposed in the liver.

The decomposition process of ethanol in liver includes conversion of ethanol into acetaldehyde through an oxidation reaction. It is known that this decomposition is carried out by three reaction enzyme systems including ADH, microsomal ethanol-oxidizing system (MEOS) and catalase (K. Ebihara et al., Agri. Biol. Chem., 52, 1311, 1988)

In addition to the decomposition mechanism of ethanol, toxicity of ethanol has also been researched. It is reported that the toxicity of ethanol is neurologically observed and induces genetic effects (J. Caballeria, et al., Life Sci., 41, 1021-1727, 1986).

Recently, many substances capable of reducing the toxicity of ethanol or preventing the expression of toxicity have been studied. In this connection, natural foods and health-aid foods containing extracts of herbal raw materials are being developed (Jung Han Kim et al., Journal of Korean Society of Agricultural Chemistry and Biotechnology, 38(6), 549-553, 1995).

As a result, compositions containing cholic acids which are widely used as cholelitholytics are commercially available. Cholic acids include ursodeoxycholic acid having a choleretic function, a liver detoxification function, a function to improve liver blood flow, a function to promote fat absorption, and a function to excrete waste materials through microbiliary tracts, thereby improving the liver-function of patients with chronic liver disease, and affecting general malaise, dyspepsia, anorexia, physical fatigue, etc. due to liver-function disorder; tauroursodeoxycholic acid, which is commercially available as cholelitholytics and is reported to treat fatty liver by improving the liver-function and reducing the amount of fat in the liver after being orally administered; chenodeoxycholic acid commercially available as cholelitholytics; dehydrocholic acid, etc.

Medicaments containing Ginseng Radix, sibberian ginseng (gasiogapi) or the like, which are known to be useful in Chinese medicaments and folk remedies for removing a katzenjammer, as a main ingredient have been developed in various forms. Many tonic drinks comprising Ginseng Radix as a main ingredient are commercially available and compositions comprising various ingredients such as honey, vitamins, etc., are commercially available as tonics. Although herbs such as Ginseng Radix, sibberian ginseng (Brekhman, Pharmacological investigation of glycosides from Ginseng and Eleutherococcus, Lloydia, volume 32, 46-51, 1969), Ocimum Sanctum Linn and Tinosporamalabarica (Sen, P., Maiti, P C and Ray, A. Mechanism of anti-stress activity of Linn, eugenol and in experimental animals, Indian J. Exp. biol., 30, 592-596, 1992), and biomaterials such as melatonin are reported to have an effect of removing a katzenjammer, they remove only some changes induced by drinking or their treatment effect is insignificant. The medicaments have no technical development in that conventional herb extracts are used. Most are used only as tonics and are developed from only known effects of ingredients.

As described above, various herbs have been used for removing a katzenjammer after drinking and various drinks containing herbs have recently become commercially available. Such drinks are taken alone after drinking or added to alcoholic drink having high alcohol content before drinking. However, some drinks containing herbs sometimes induce general malaise, abdominal distension, emesis or abdominal pain are expensive due to the inclusion of expensive herbs.

Thus, there is a need for a composition for effectively removing katzenjammer, in particular, a composition for removing a katzenjammer in which herb extracts are properly formulated to exert good effects in the prevention or treatment of a katzenjammer and excellent liver-protection are required.

The present inventors studied herbs having good effects in the prevention and treatment of a katzenjammer and discovered that each extract of *Rosa roxburghii*, *Engelhardtia chrysolepis* HANCE and *Nelumbo nucifera* has effects of preventing and treating a katzenjammer and a composition comprising these ingredients in proper amounts has excellent effects of preventing and treating a katzenj ammer.

*Rosa roxburghii* is a plant belonging to Rosaceae and is also called a sweet chestnut rose. *Rosa roxburghii* is distributed in eastern Asia, China, Himalaya, etc., and its fruit and seeds are edible. It has been used as a food for health aid and beauty in Guizhou province in China and as a beverage for preventing ageing, freckles and wrinkles in Japan due to its enriched vitamin and potent superoxide dismutase activity.

Korean Patent Publication No. 2000-0021322 discloses a stress releasing drink comprising a rose extract. The stress releasing drink contains a rose fruit extract, extracted with ethanol/1,3-butyleneglycol/purified water in the ratio of 7/1/3 (v/v/v), as a main ingredient and 10 kinds of food additives including soybean germ, bamboo shoots, etc. This drink effectively inhibits the generation of active oxygen such as the superoxide radical ($O_2$.) and the hydroxy radical (.OH), which promote ageing, and removes the resulting active oxygen. When a drink containing 0.1% of the rose extract is administered, MHPG-SO4 and corticosterone, which is increased due to physical and mental stress, are reduced by 17% and 25%, respectively, compared to when the drink is not administered. When a drink containing 0.5% of the rose extract is administered, MHPG-SO4 and corticosterone are reduced by 20% and 38%, respectively.

*Engelhardtia chrysolepis* HANCE is a plant belonging to Juglandaceae and is generally called Taiwan engelhardtia. *Engelhardtia chrysolepis* HANCE is distributed in south and southwest districts in China and its leaf is edible. It has sweet taste, and thus has been used to produce a sweet tea and a health aid tea in China for many centuries. In Japan, it is called Kohki tea and is drunk in the form of a drink or a tea.

*Nelumbo nucifera* belongs to Nymphaeaceae and is called a lotus flower. It mainly grows for aesthetics in lotus ponds in middle and lower districts in Korea and is distributed in India, China, Japan and Siberia. Its leaf, fruit, rhizoma and seed are edible. The seed, Nelumbines Semen is effective as a tonic and a sedative, and in invigorating the spleen and has an antidiarrhetic function, calms and nourishes the spirit, and prevents long-term diarrhea, nocturnal emission, morbid leukorrhea, palpitation and insomnia. The leaf has an antipyretic or detoxification function. The fruit is effective as a tonic and a hemostatic, and in the treatment of nocturnal enuresis and women's diseases. The root is useful for antipyresis and detoxification, removing stagnant blood, and treating blood problems, hematuria, and enterorrhagia and hemostasis.

Korean Patent Publication No. 2004-0026175 discloses an analgesic comprising *Nelumbo nucifera* as an effective ingredient, which may alleviate general pain as well as pain due to damage to nerves.

Korean Patent Publication No. 2003-0079104 discloses a *Nelumbo nucifera* extract for treating depression, a method of preparing the same, a pharmaceutical composition and a health food comprising the extract. More particularly, the *Nelumbo nucifera* extract extracted using alcohol or an aqueous alcohol solution shows a potent antidepressant action and ensures safety as a natural medicament, and thus can be useful as a composition for treating depression and as a health food.

Korean Patent Publication No. 2003-0031729 discloses a *Nelumbo nucifera* extract for protecting hepatocyte and preventing and treating hepatic damage, and a composition for protecting hepatocyte, preventing and treating hepatic damage, and inhibiting mutation by a hepatoma inducing material comprising the extract as an effective ingredient.

DETAILED DESCRIPTION OF THE INVENTION

Technical Goal of the Invention

Figure 1:
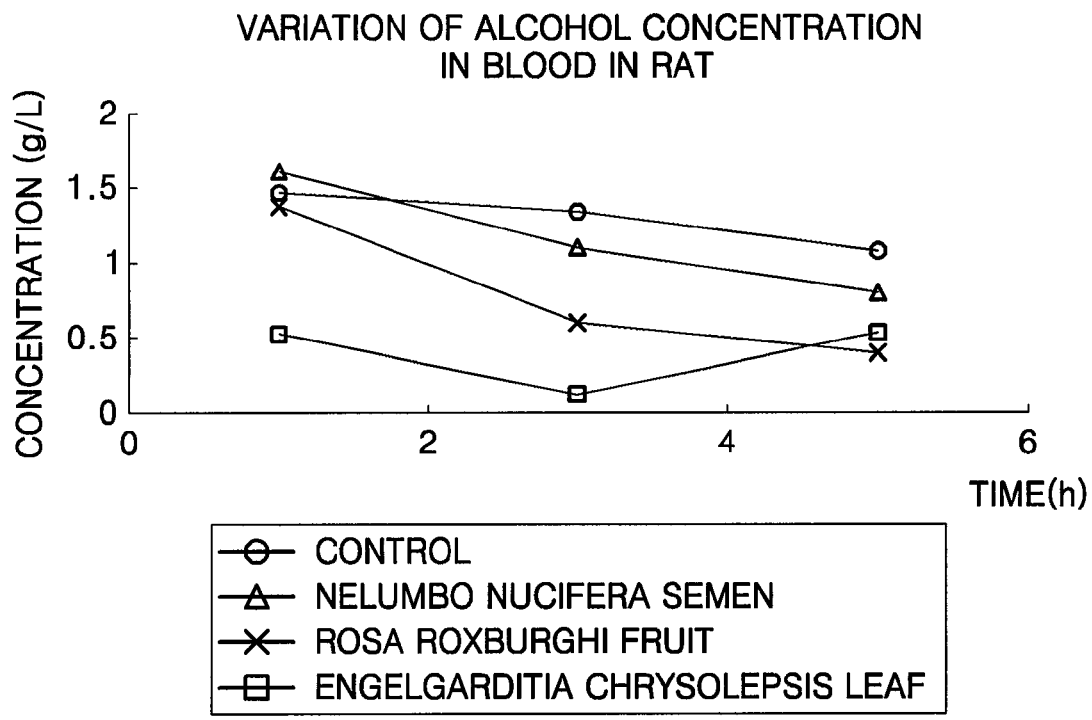
FIG. 1 is a graph of the concentration of alcohol in blood with respect to time when hot water extracts of *Rosa roxburghii* fruit, *Engelhardtia chrysolepis* HANCE leaf and *Nelumbo nucifera* semen are respectively administered to rats.

The present invention provides a composition for preventing and treating katzenj ammers.

Disclosure of the Invention

According to an aspect of the present invention, there is provided a composition for preventing and treating katzenjammers, including at least one extract selected from the group consisting of a *Rosa roxburghii* extract, an *Engelhardtia chrysolepsis* HANCE extract, a *Nelumbo nucifera* extract, and a combination thereof as an active ingredient.

According to another aspect of the present invention, there is provided a composition for preventing and treating katzenjammer, including 25-50 parts by weight of an *Engelhardtia chrysolepsis* HANCE extract and 25-50 parts by weight of a *Nelumbo nucifera* extract with respect to 100 parts by weight of a *Rosa roxburghii* extract.

According to another aspect of the present invention, there is provided a method of preparing a composition for preventing and treating katzenjammers. The method includes: individually extracting *Rosa roxburghii*, *Engelhardtia chrysolepsis* HANCE, and *Nelumbo nucifera* using hot water; filtering and centrifuging the hot water extracts to separate supernatants; concentrating the supernatants in a vacuum to obtain concentrates; spray drying the concentrates to obtain extract powders; and mixing the extract powders in a certain ratio.

Hereinafter, the present invention will be described in greater detail.

To find a material having the effect of removing katzenjammers, the present inventors studied effects of various materials to reduce alcohol concentration and acetaldehyde concentration in blood. As a result, it was found that *Rosa roxburghii*, *Engelhardtia chrysolepsis* HANCE and *Nelumbo nucifera* have the effect of reducing the concentration of alcohol in blood. Further, it was found that these materials also have the effect of reducing the concentration of acetaldehyde, which is another material inducing katzenjammer, in blood. Extracts of *Rosa roxburghii*, *Engelhardtia chrysolepsis* HANCE and *Nelumbo nucifera* have been proven to have the effect of reducing concentrations of alcohol and acetaldehyde, which induce katzenjammers in blood, and thus can be used as food or medicaments for preventing and treating katzenjammers.

A composition including 25-50 parts by weight of the *Engelhardtia chrysolepsis* HANCE extract and 25-50 parts by weight of the *Nelumbo nucifera* extract with respect to 100 parts by weight of the *Rosa roxburghii* extract has a significant effect in the prevention and treatment of katzenj ammers.

The composition for preventing and treating katzenjammers can be used as a pharmaceutical composition. In this case, a general formulation is prepared using the composition for preventing and treating katzenjammers and other pharmaceutical acceptable carriers and additives.

Examples of the carrier include a diluent, a lubricant, a binder, a disintegrating agent, a sweetening agent, a stabilizer and a preservative and examples of the additive include a flavoring agent, vitamins and an antioxidant.

The pharmaceutical composition can be orally administered in the form of a solution, a suspension, a powder, a granule, a tablet, a capsule, a pill or an extract, but is not limited thereto.

Any pharmaceutically acceptable carrier and additive can be used. The diluent includes lactose, corn starch, soybean oil, microcrystalline cellulose or mannitol; the lubricant includes magnesium stearate or talc; and the binder includes polyvinylpyrollidone or hydroxypropylcellulose. The disintegrating agent includes calcium carboxymethylcellulose, sodium starch glycolate, potassium polyacrylate, or crospovidone; the sweetening agent includes white sugar, fructose, sorbitol or aspartame; the stablizaer includes sodium carboxymethylcellulose, β-cyclodextrine, or Xhantan gum; and the preservative includes methyl parahydroxybenzoate, propyl parahydroxybenzoate or potassium sorbate.

The pharmaceutical composition may further include auxiliaries such as vitamins B, C, E or β-carotine; minerals such as Ca, Mg and Zn; phospholipids such as Lecithin; or maltol, fructose, oligosaccharide, amino acid, *Ganoderma Lucidum* (GL), taurine, etc. In addition to these ingredients, known additives for improving flavor, for example, a natural flavouring agent such as plum, lemon, pineapple or herb flavor; a natural fruit juice; a natural dye such as chlorophyllin or flavonoid; a sweetening component such as fructose, honey, sugar alcohol, or sugar; or an acidulant such as citric acid or sodium citrate may also be included.

In the pharmaceutical composition for preventing and treating katzenjammers, the effective amount of the main ingredient is in the range of 5 mg to 15 g, preferably 50 mg to 15 g, per day for an adult with a body weight of 60 kg and is once or several times daily administered orally.

Also, the composition for preventing and treating katzenjammers can be used as a health aid food. The health aid food can be prepared in the form of a tea, a jelly, an extract, a beverage, etc., comprising extracts of the above medicinal plants as effective ingredients. Various health aid foods of the present invention prevent or remove katzenjammers without side-effects and can be easily administered.

The composition for preventing and treating katzenjammers may be prepared by mixing the above herb extracts. Specifically, a method of preparing the composition including 25-50 parts by weight of the *Engelhardtia chrysolepsis* HANCE extract and 25-50 parts by weight of the *Nelumbo nucifera* extract with respect to 100 parts by weight of *chrysolepsis* HANCE, and *Nelumbo nucifera* using hot water; filtering and centrifuging the hot water extracts to separate supernatants; concentrating the supernatants in a vacuum to obtain concentrates; spray drying the concentrates to obtain extract powders; and mixing the extract powders in a certain ratio.

The extraction is preferably carried out by placing 5-15 parts by weight of water together with 1 part by weight of each herb in an extractor and extracting the herbs at 90-100° C. for 1-2 hours.

However, the method of preparing the composition for preventing and treating katzenjammer is not limited to the above-described method and can be partially modified using extraction methods of herbs known in the art.

Effect of the Invention

Each extract of the *Rosa roxburghii*, the *Engelhardtia chrysolepsis* HANCE and *Nelumbo nucifera*, and the composition containing them can reduce concentrations of alcohol and acetaldehyde in blood, and thus can be used as a medicament or a health aid food for preventing or removing katzenjammers which are induced by alcohol or acetaldehyde.

BEST MODE FOR CARRYING OUT THE INVENTION

The present invention will now be described in greater detail through the following examples.

Examples 1

Preparation of extract powders of *Rosa roxburghii, Engelhardtia chrysolepsis* HANCE and *Nelumbo nucifera* 200 g of each of the *Rosa roxburghii* fruit, the *Engelhardtia chrysolepsis* HANCE leaf and *Nelumbo nucifera* semen was extracted with 2 L of hot water at 95° C. for 2 hours. The resultant was filtered through a filter paper to obtain 400 g of extract. The extract was let alone for 12 hours and a supernatant was taken. The supernatant was concentrated in a vacuum to obtain a concentrate containing 50% solids. The concentrate was spray dried to obtain an extract powder.

Example 2

Preparation of composition for preventing and treating katzenjammers 0.002 g of vitamin B1, 0.002 g of vitamin B2, 1 g of alanine, 10 g of honey, 113.4 g of fructose, 0.5 g of *Ganoderma Lucidum* (GL), and 20.1 g of taurine were added to 2 g of the *Rosa roxburghii* extract powder, 0.5 g of *Engelhardtia chrysolepsis* HANCE extract powder and 0.5 g of *Nelumbo nucifera* extract powder, and then a proper amount of water was added thereto to obtain a 1 L composition. The resultant was divided into 100 mL amounts and put in aluminum pouches and sterilized in boiling water for 5 minutes.

Experimental Example 1

Determination of Activity of Alcohol Dehydrogenase (ADH)

The activity of ADH was determined using a modified Blandino method and a rate of generating NADH at an absorbance of 340 nm was used as a reference. A mixed solution containing 1.4 ml of distilled water, 0.75 ml of 1.0 M Tris-HCl buffer (pH 8.8), 0.3 ml of 20 mM $NAD^+$, 0.3 ml of ethanol, and 0.1 ml of each concentrate obtained in Example 1 as a sample was placed together with 0.15 ml of an enzyme source in a cuvette to form a 3 mL mixture, and then preincubation was performed at 30° C. for 5 minutes. Then, absorbance was measured at 340 nm for 5 minutes. A control group did not contain the sample.

The ADH activity of the sample was determined from the relative activity (%) of the mixture containing each concentrate obtained in Example 1 as a sample with respect to the control group.

The experimental results are indicated in Table 1. As is apparent from Table 1, all of the *Rosa roxburghii* fruit, the *Engelhardtia chrysolepsis* HANCE leaf and the *Nelumbo nucifera* semen increased the ADH activity.

Experimental Example 2

Determination of Activity of Acetaldehyde Dehydrogenase (ALDH)

The activity of ALDH was determined using a modified Bostian method and a rate of generating NADH at an absorbance of 340 nm was used as a reference. A mixed solution containing 2.1 ml of distilled water, 0.3 ml of 1.0M Tris-HCl buffer (pH 8.0), 0.1 ml of 20 mM NAD$^+$, 0.1 ml of 1.0M acetaldehyde, 0.1 ml of 3.0M KCl, 0.1 ml of 0.33M 2-mercaptoethanol and 0.1 ml of each concentrate obtained in Example 1 as a sample was placed together with 0.1 ml of an enzyme source in a cuvette to form a 3 mL mixture, and then preincubation was performed at 30° C. for 5 minutes. Then, an absorbance was measured at 340 nm for 5 minutes. A control group did not contain the sample.

The ALDH activity of the sample was determined from the relative activity (%) of the mixture containing the sample with respect to the control group.

The experimental results are indicated in Table 1. As is apparent from Table 1, the *Nelumbo nucifera* extract effectively increases the ALDH activity.

TABLE 1

| Herb | ADH | ALDH |
|---|---|---|
| *Rosa roxburghi* fruit | 114.71 | 100.38 |
| *Engelgarditia chrysolepsis* HANCE leaf | 108.6 | 85.14 |
| *Nelumbo nucifera* semen | 127.88 | 105.51 |

Experimental Example 3

Measuring of Concentration of Alcohol in Blood

Male Wistar rats weighing 200-250 g were pre-reared by being allowed to freely drink tap water and eat solid samples for 2 weeks. After the pre-rearing was finished, the rats were provided with only water and no food for 24 hours before the experiment. The starved rats were orally administered with a 2% solution of *Rosa roxburghii* extract powder, a 0.5% solution of *Engelhardtia chrysolepsis* HANCE extract powder and a 0.5% solution of *Nelumbo nucifera* extract powder prepared in Example 1 and the composition of Example 2, respectively, using a stomach sonde at a dosage of 200 mg/kg.

After 30 minutes, ethanol was orally administered at a dosage of 3 g/kg. Blood was collected from the orbit 1 hour and 3 hours after administration of ethanol and blood was collected from the heart 5 hours after administration of ethanol. The collected blood was centrifuged at 3000 rpm for 10 minutes and serum was separated. The content of ethanol in the serum was analyzed using F-kit ethanol (Roche Diagnostics Corporation).

For reference, the functional principle and kit protocol of the F-kit ethanol are as follows:

*Principle

Ethanol is oxidized by the enzyme ADH in the liver to form acetaldehyde. In this process, NADH is produced in the presence of NAD$^+$ as a coenzyme. The amount of NADH is measured at an absorbance of 340 nm.

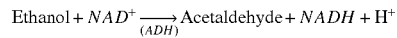

$$\text{Ethanol} + NAD^+ \xrightarrow[(ADH)]{} \text{Acetaldehyde} + NADH + H^+$$

Kit Protocol
1) Mix 3 ml of a reaction mixture (potassium phosphate buffer (pH9)+purified NAD$^+$) with 0.1 ml of 10 times diluted blood.
2) Incubate the mixture at 20° C. for 3 minutes.
3) Measure absorbance (A1) at 340 nm.
4) Add 0.005 ml of ADH
5) Incubate the resultant at 20° C. for 5 minutes.
6) Measure absorbance (A2) at 340 nm.
☐ Concentration=0.7259/3×ΔA
ΔA=sampled (A2−A1)

Figure 2:
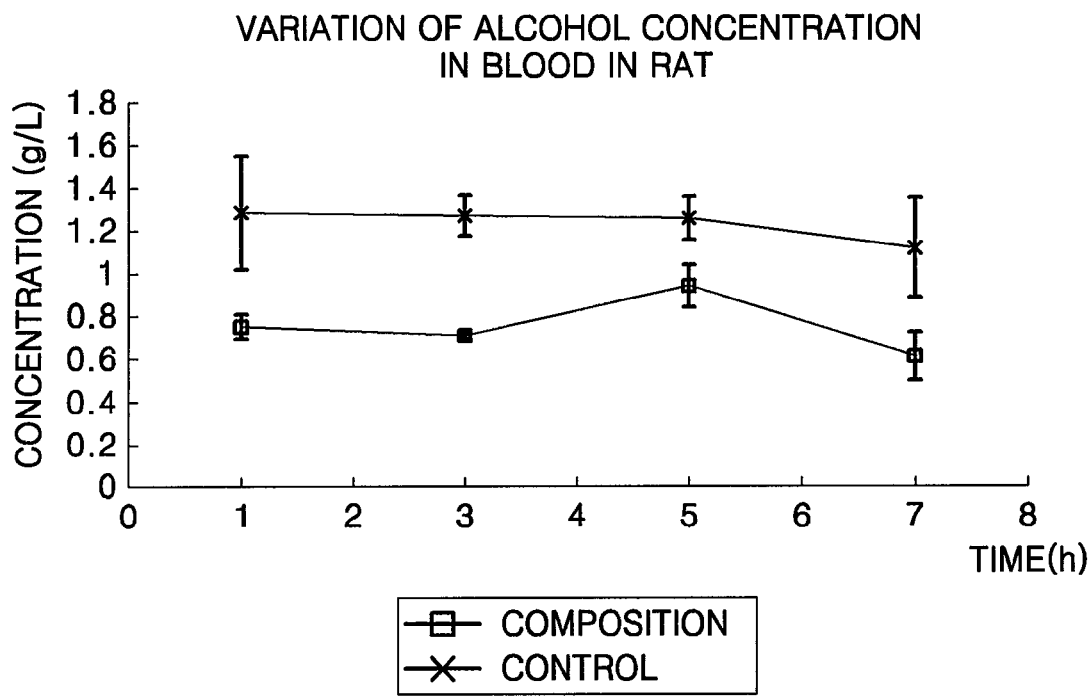
FIG. 2 is a graph of the concentration of alcohol in blood with respect to time when a composition for preventing and treating katzenjammers comprising hot water extracts of *Rosa roxburghii* fruit, *Engelhardtia chrysolepis* HANCE leaf and *Nelumbo nucifera* semen is administered to a rat.

The obtained results are illustrated in FIGS. 1 and 2. Referring to FIGS. 1 and 2, the extracts of the *Rosa roxburghii* fruit, the *Engelhardtia chrysolepsis* HANCE leaf and the *Nelumbo nucifera* semen of Example 1 and the composition of Example 2 significantly reduce the alcohol concentration to the control group.

Experimental Example 4

Measuring of Concentration of Acetaldehyde in Blood

Male Wistar rats weighing 200-250 g were pre-reared by being allowed to freely drink tap water and eat solid samples for 2 weeks. After the pre-rearing was finished, the rats were provided with only water and no food for 24 hours before experiment. The starved rats were orally administered with a 2% solution of *Rosa roxburghii* extract powder, a 0.5% solution of *Engelhardtia chrysolepsis* HANCE extract powder and a 0.5% solution of *Nelumbo nucifera* extract powder prepared in Example 1 and the composition of Example 2 using a stomach sonde at a dosage of 200 mg/kg.

After 30 minutes, ethanol was orally administered at a dosage of 3 g/kg. Blood was collected from the orbit 1 hour and 3 hours after administration of ethanol and blood was collected from the heart 5 hours after administration of ethanol. The collected blood was centrifuged at 3000 rpm for 10 minutes and serum was separated. The content of acetaldehyde in serum was analyzed using F-kit acetaldehyde (Roche Diagnostics Corporation).

For reference, the functional principle and kit protocol of the F-kit acetaldehyde are as follows.
* Principle Acetaldehyde is oxidized by the enzyme ALDH in the liver to form acetic acid. In this process, NADH is produced in the presence of NAD$^+$ as a coenzyme. The amount of NADH is measured at an absorbance of 340 nm.

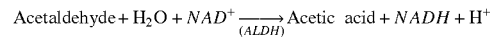

$$\text{Acetaldehyde} + H_2O + NAD^+ \xrightarrow[(ALDH)]{} \text{Acetic acid} + NADH + H^+$$

Kit protocol
1) Mix 3 ml of a reaction mixture (potassium phosphate buffer (pH 9)+purified NAD$^+$) with 0.2 ml of 10 times diluted blood.
2) Incubate the mixture at 20° C. for 3 minutes.
3) Measure absorbance (A1) at 340 nm.

4) Add 0.05 ml of ALDH.
5) Incubate the resultant at 20° C. for 5 minutes.
6) Measure absorbance (A2) at 340 nm.
☐ Concentration=0.7158/3.6×ΔA
ΔA=sample (A2−A1)−blank test (A2−A1)

Figure 3:
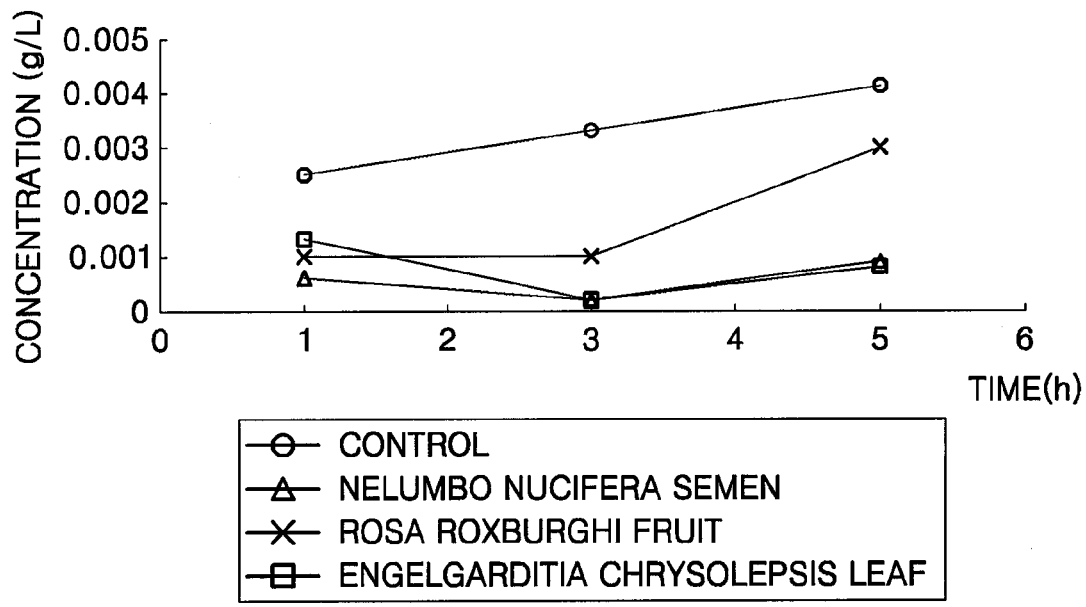
FIG. 3 is a graph of the concentration of acetaldehyde in blood with respect to time when hot water extracts of *Rosa roxburghii* fruit, *Engelhardtia chrysolepis* HANCE leaf and *Nelumbo nucifera* semen are respectively administered to rats.
Figure 4:
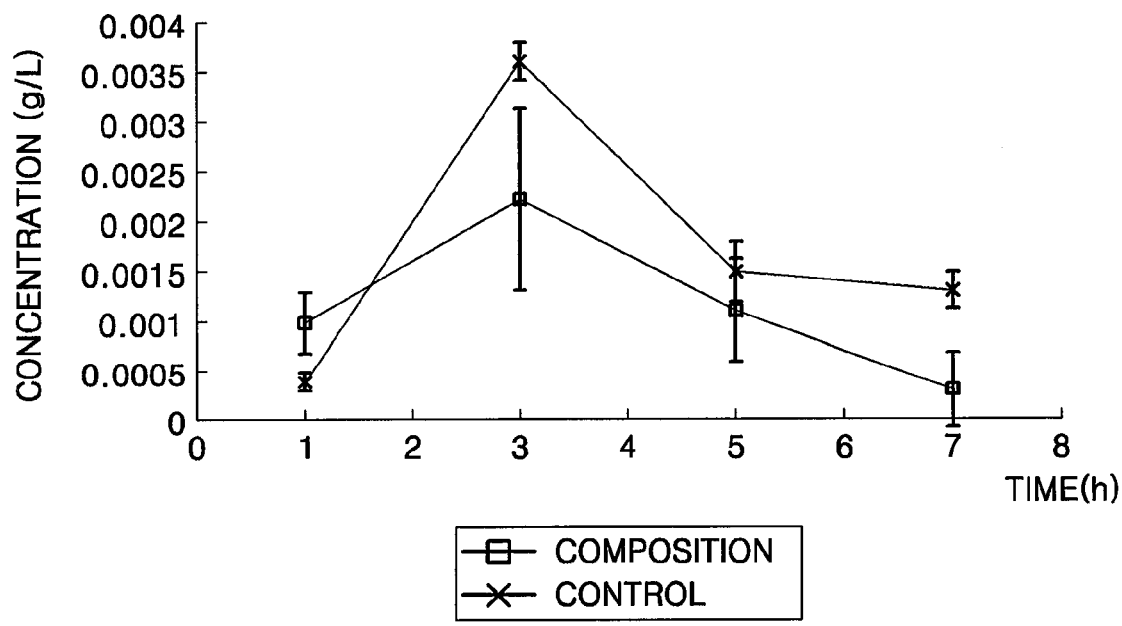
FIG. 4 is a graph of the concentration of acetaldehyde in blood with respect to time when a composition for preventing and treating katzenjammers comprising hot water extracts of *Rosa roxburghii* fruit, *Engelhardtia chrysolepis* HANCE leaf and *Nelumbo nucifera* semen is administered to a rat.

The obtained results are illustrated in FIGS. 3 and 4. Referring to FIGS. 3 and 4, the extracts of the *Rosa roxburghii* fruit, the *Engelhardtia chrysolepsis* HANCE leaf and the *Nelumbo nucifera* semen of Example 1 and the composition of Example 2 significantly reduced the acetaldehyde concentration compared to the control group.

Experimental Example 5

Measuring of Concentration of Alcohol in Blood

Male Wistar rats weighing 200-250 g were pre-reared by being allowed to freely drink tap water and eat solid samples for 2 weeks. After the pre-rearing was finished, the rats were provided with only water and no food for 24 hours before experiment. The *Rosa roxburghii* extract, the *Engelhardtia chrysolepsis* HANCE extract and the *Nelumbo nucifera* extract of Example 1 and yeast extract (Kyowa Fermentation, glutayeast) were mixed as indicated in Table 2 to prepare aqueous solutions and orally administered to the starved rats using a stomach sonde at a dosage of 200 mg/kg.

After 30 minutes, ethanol was orally administered at a dosage of 3 g/kg. Blood was collected from the orbit 1 hour and 3 hours after administration of ethanol and blood was collected from the heart 5 hours after administration of ethanol. The collected blood was centrifuged at 3000 rpm for 10 minutes and serum was separated. The content of ethanol in serum was analyzed using F-kit ethanol (Roche Diagnostics Corporation).

Figure 5:
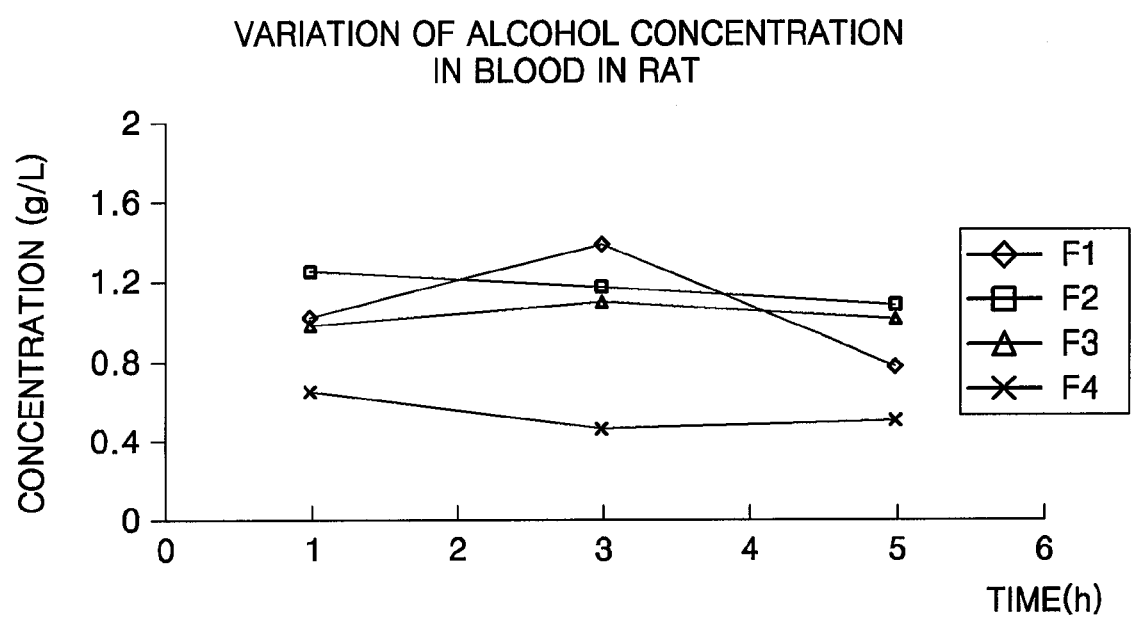
FIG. 5 is a graph of the concentration of alcohol in blood with respect to time when various combinations of extracts of *Rosa roxburghii* fruit, *Engelhardtia chrysolepis* HANCE leaf, *Nelumbo nucifera* semen and yeast are administered to rats.

The obtained results are illustrated in FIG. 5. Referring to FIG. 5, when concentrations of the *Rosa roxburghi* extract, the *Engelgarditia chrysolepsis* HANCE extract and the *Nelumbo nucifera* extract are 2 wt %, 0.5 wt % and 0.5 wt %, respectively, the concentration of alcohol in blood is significantly reduced compared to other cases.

TABLE 2

| | *Rosa roxburghi* | *Engelgarditia chrysolepsis* HANCE | *Nelumbo nucifera* | Yeast essence |
|---|---|---|---|---|
| F1 | 2 wt % | — | 1 wt % | 2 wt % |
| F2 | 2 wt % | — | 1 wt % | 1 wt % |
| F3 | 2 wt % | — | 1 wt % | — |
| F4 | 2 wt % | 0.5 wt % | 0.5 wt % | — |

The invention claimed is:

1. A composition for treating hangover in a subject, consisting essentially of a combination of a *Rosa roxburghii* extract, an *Engelhardia chrysolepis* HANCE extract, and a *Nelumbo nucifera* extract as active ingredients and at least one carrier or excipient.

2. The composition of claim 1, wherein the amount of the *Engelhardia chrysolepis* HANCE extract is 25-50 parts by weight and the amount of the *Nelumbo nucifera* extract is 25-50 parts by weight of the *Rosa roxburghii* extract.

3. The composition of claim 1 in the form of a solution, a suspension, a powder, a granule, a tablet, or a capsule.

4. The composition of claim 1, wherein said subject is planning to consume beverages comprising ethanol or has consumed beverages comprising ethanol.

5. The composition of claim 1, wherein the *Rosa roxburghii* extract, the *Engelhardia chrysolepis* HANCE extract, and the *Nelumbo nucifera* extract are hot water extracts.

6. A composition for treating hangover in a subject, the composition consisting essentially of a combination of a *Rosa roxburghii* extract, an *Engelhardia chrysolepis* HANCE extract, and a *Nelumbo nucifera* extract as active ingredients and at least one carrier selected from the group consisting of microcrystalline cellulose, polyvinylpyrrolidone, hydroxypropylcellulose, calcium carboxymethylcellulose, sodium carboxymethylcellulose, potassium polyacrylate, crospovidone, and β-cyclodextrin.

\* \* \* \* \*